US006553319B1

United States Patent
Helffrich et al.

(10) Patent No.: US 6,553,319 B1
(45) Date of Patent: Apr. 22, 2003

(54) UNATTENDED LIQUID SAMPLE MONITORING AND LIQUID SAMPLE STORAGE SYSTEM

(75) Inventors: Jerome A. Helffrich, San Antonio, TX (US); William G. McBride, Jr., San Antonio, TX (US)

(73) Assignee: Southwest Research Institute, San Antonio, TX (US)

( * ) Notice: Subject to any disclaimer, the term of this patent is extended or adjusted under 35 U.S.C. 154(b) by 23 days.

(21) Appl. No.: 09/902,022

(22) Filed: Jul. 10, 2001

(51) Int. Cl.[7] .............................................. G06F 19/00
(52) U.S. Cl. ........................................ 702/25; 702/23
(58) Field of Search ................... 702/23, 25; 73/194 E; 204/153.1, 406; 128/632; 250/343; 324/29, 321, 694; 340/853.3; 364/496, 497; 436/52; 600/309

(56) References Cited

U.S. PATENT DOCUMENTS

| | | | | |
|---|---|---|---|---|
| 3,934,471 A | * | 1/1976 | White et al. ............... | 73/194 E |
| 4,478,222 A | | 10/1984 | Koning et al. .............. | 128/632 |
| 4,801,805 A | | 1/1989 | Butler et al. ................. | 250/343 |
| 4,958,295 A | * | 9/1990 | Davidson et al. ........... | 364/497 |
| 5,260,667 A | | 11/1993 | Garcia-Golding et al. .. | 324/694 |
| 5,336,388 A | | 8/1994 | Leader et al. ............... | 204/406 |
| 5,397,989 A | | 3/1995 | Spraul et al. ................ | 324/321 |
| 5,405,510 A | | 4/1995 | Betts et al. .............. | 204/153.1 |
| 5,646,863 A | * | 7/1997 | Morton ....................... | 364/496 |
| 5,948,684 A | | 9/1999 | Weigl et al. .................... | 436/52 |
| 5,976,085 A | | 11/1999 | Kimball et al. ............. | 600/309 |
| 6,356,205 B1 | * | 3/2002 | Salvo et al. ............. | 340/853.3 |

OTHER PUBLICATIONS

Drost, S; Worman, W; Woias, P; Ross, B; Koster, O; Konz, W; Edler, B; Schuhmann, W; Meixner, L; Ferretti, R; "Microanalytical System For Environmental Control"; International Conference on Solid State Sensors and Actuators; vol. 2; 1997; pp. 931–934.*

Hesketh, P J; Zivanovic, S; Ming, Y; Park, S; Svojanovsky, S; Cunneen, J; Caraffini, S; Boyd, J G; Stetter, J R; Lunte, S M; Wilson, G S; "Microfabricated Biosensors And Microsystems"; Int'l Conf Proceedings on Microelectronics; 1997; vol. 1; pp. 63–69.*

Knauth, H D; Schroeder, F; "Automatic Monitoring And Sampling Of Harmful Substances In Estuaries And Coastal Waters"; Oceans Proceedings; 1994; vol. 3; pp. III/303–III/307.*

Leppanen, J M; Rantajarvi, E; Maunumaa, M; Larinmaa, M; Pajala, J; "Unattended Algal Monitoring System—A High Resolution Method For Detection Of Phytoplankton Blooms In The Baltic Sea"; Oceans Proceedings; 1994; vol. 1; pp. I/461–I/463.*

* cited by examiner

Primary Examiner—John Barlow
Assistant Examiner—Douglas Washburn
(74) Attorney, Agent, or Firm—Baker Botts L.L.P.

(57) ABSTRACT

An unattended, self-calibrating, microprocessor controlled, electromechanical liquid sample acquisition, analysis and storage system is contained in a sealed evacuated housing. Liquid is drawn by suction into the sealed evacuated housing where it passes through a microfluidic manifold assembly to be brought into contact with signal producing liquid condition sensors. A marker solution is used to demarcate samples of liquid stored in an evacuated capillary. The microprocessor stores the signals produced by the liquid condition sensors and allows for cross-referencing the stored signals with the stored liquid samples in the capillary.

30 Claims, 1 Drawing Sheet

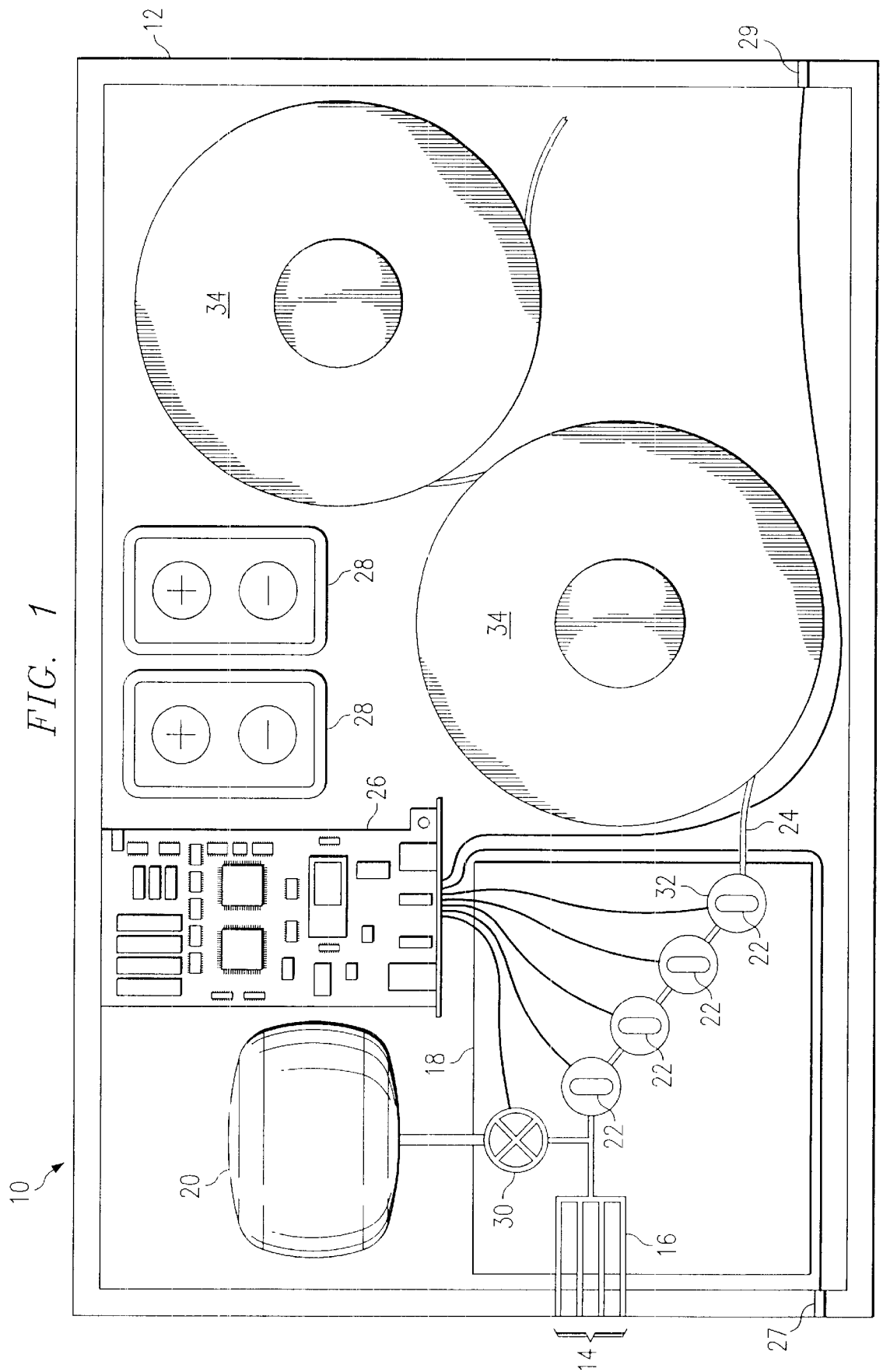

UNATTENDED LIQUID SAMPLE MONITORING AND LIQUID SAMPLE STORAGE SYSTEM

TECHNICAL FIELD OF THE INVENTION

This invention relates to the field of liquid sample analysis; more particularly, the present invention addresses the problems of monitoring the properties of liquids in inaccessible areas.

BACKGROUND OF THE INVENTION

When monitoring liquid flows for indications of contamination, it is frequently necessary to get as close as possible to the source of contamination to maximize the probability for accurately detecting the contamination. Getting as close as possible to a source of contamination leads to physical accessibility issues, which can best be mitigated by making only two visits—one visit to leave a liquid sample monitoring system in place and one visit to retrieve it. Prior art liquid flow monitoring systems have suffered from either the inability to pinpoint when the contamination occurred or the inability to monitor continuously for extended periods of time.

Electromechanical liquid monitoring devices are not new in the prior art. Typically, prior art electromechanical liquid monitoring devices have been designed for a limited use and include features specifically directed to the specific liquid being measured and the degree of measurement accuracy required.

Exemplary of prior art electromechanical liquid monitoring devices are the following:

U.S. Pat. No. 4,039,933 describes an instrument for blood chemistry analysis. Key to the operation of the disclosed instrument are the automatic calibration electronics. Not included in the disclosed invention are any provisions for liquid flow control or storage of the liquid samples analyzed by the instrument.

U.S. Pat. No. 4,478,222 describes an instrument that utilizes a reference liquid flow passage in its body portion. Electromechanical sensors, such as ISFET (ion selective field effect transistor) devices are used for sensing the presence of a particular ion in the analyzed liquid. U.S. Pat. No. 5,405,510 describes a portable liquid analysis system. U.S. Pat. No. 5,976,085 describes a liquid analysis system that uses electrical control of on-board valves to alter the flow of blood through the analysis system. The Monterey Bay Aquarium Research Institute (MBARI) developed a device called the Osmo Sampler, which was first described in 1991 at an IEEE (Institute for Electronic and Electrical Engineers) meeting. In the Osmo Sampler, a sample of sea water was reacted with chemical reagents while it was contained inside a capillary. Color changes were detected in situ. The color changes were used to identify the presence of nitrate ions in the sampled sea water. The Osmo Sampler used osmosis to drive the sea water through the system and perform a continuous analysis. Later versions of the Osmo Sampler were designed for deployment and retrieval after unattended operation.

SUMMARY OF THE INVENTION

The present invention describes an unattended, self calibrating, microprocessor controlled, electromechanical liquid sample monitoring and liquid sample storage system.

The disclosed liquid sample monitoring and liquid sample storage system is designed to facilitate remote liquid quality monitoring by being both portable and capable of many months of unattended operation. Specifically, the disclosed system includes a filtered inlet, a microfluidic manifold having a pressurized reference liquid injector system and sensors for the measurement of various liquid parameters, one or more parallel long glass capillaries and a microprocessor assembly with analog-to-digital converters and a non-volatile memory. The entire liquid sample monitoring and liquid sample storage system is enclosed in an evacuated housing.

At the end of the desired liquid monitoring period, the system is retrieved and the critical sensor measurements are uploaded from the onboard microprocessor. Additional information about the properties of the liquid sampled may be obtained by breaking the capillary open and subjecting the liquid samples stored within the capillary to a full laboratory analysis. The capillary is physically filled with the liquid being sampled by slow suction into a pre-evacuated volume, thus eliminating the power requirements and complexity of a mechanical pump for drawing the liquid to be analyzed into the system.

The design of the system facilitates long-term unattended operation. The properties of liquids may be monitored continuously such that the presence of rare and/or brief transient contaminants in the liquid flow are not missed.

BRIEF DESCRIPTION OF THE DRAWINGS

FIG. 1 illustrates a liquid sample monitoring device in accordance with the invention.

DETAILED DESCRIPTION OF THE INVENTION

While the following description of the invention indicates its use in monitoring and storing samples of water, those of ordinary skill in the art will understand the applicability of the present invention to a wide variety of liquids. Typically, the device is completely immersed in a body of the liquid of interest.

The following description is directed to a device that combines the functionality of a computerized data logger with the functionality of a water sampling device, taking advantage of the best features of both. The microprocessor controlled water quality sensors of the liquid sample monitoring and liquid sample storage system of the present invention provide quick access to the measured and recorded data (water condition parameters such as pH, turbidity, and chloride concentration). They may for example be used to provide information as to whether threshold levels for these parameters have been exceeded during the deployment of the system in a remote area suspected of being a site for the dumping of contaminants into a stream of flowing water. Capillaries within the system store physical evidence of the occurrence of a detected contamination event. An electronic record can be used as an alarm of a contamination event and thus indicate the need for a more elaborate analysis of the contents of the water storage capillary.

Referring to FIG. 1, the unattended liquid sample monitoring and liquid storage system 10 of the present invention has a housing 12, which is a sealed vacuum chamber with the electronics and liquid passages contained therein. The sealed housing 12 is placed with at least the inlet 14 in the flow of water to be sampled. If desired, the sealed housing 12 may be completely immersed in the water flow. When an external plug (not shown) is removed from inlet 14, the water flow being analyzed flows through the inlet filter 16 and into the microfluidic manifold assembly 18. The microfluidic manifold assembly 18 is connected to a pressurized volume of reference liquid 20 that both periodically calibrates the water condition sensors 22 and back-flushes the inlet filter 16 to keep it from becoming clogged by debris contained in the water flow.

A continuous low flow of water is drawn in the housing 12 by a vacuum. The continuous low flow of water is directed through the microfluidic manifold assembly 18 and then into the water sample storage capillary 24. While passing through the microfluidic manifold assembly 18, the water being sampled flows past the array of water condition sensors 22. For example these water condition sensors 22 may be ISFET sensitive to pH or to the presence of chloride ions, K+ ions and $NO_3$ ions in the water. In general, the water condition sensors 22 contact with the water flow being analyzed and could be based on optical, acoustic, electric, or magnetic field transmission through the water or a substrate exposed to the water being sampled. Alternatively, biologically selective sensors may be employed. One example of a biologically selective sensor is a surface acoustic wave resonator whose face is sensitized with antigens or DNA fragments from cryptosporidia.

In the preferred embodiment, the microfluidic manifold assembly 18 is made of a sandwich of rubber between either acrylic or glass. Alternatively, the microfluidic manifold assembly 18 may be etched directly into the acrylic or glass. The transparency of either acrylic or glass may be utilized to monitor the turbidity of the water by light transmission through the water sample itself. The microfluidic manifold assembly 18 generally serves as a mounting plate for the array of water condition sensors 22 and an adapter fitting to the water sample storage capillaries 24.

The electronic outputs from the array of water condition sensors 22 are digitized and calibrated under the control of a low-power microprocessor assembly 26 powered by onboard batteries 28. The low-power microprocessor assembly 26 is also utilized to collect water temperature readings from a thermometer 27 and pressure readings from a pressure sensor 29 (which are examples of physical parameters not maintained by storage in the capillary). The low-power microprocessor assembly 26 also controls a subsystem which directs the injection of a visible marker and reference solution through a valve 30 into the water sample being analyzed. The opening of the valve 30 enables a pressurized volume of the marker and reference solution to flow from the pressurized volume of reference liquid 20 into the water sample at periodic time intervals. Alternatively, a visible marker and reference solution may be injected in the water sample whenever a predetermined signal level from one or more of the array of water quality sensors 22 has been exceeded. If desired, the microprocessor assembly 26 may be used to control a valve similar to valve 30 located at the inlet 14 of the housing 12 to allow water into the housing 12 at either predetermined times or on the occurrence of a signal event.

The release of solution from the pressurized volume of reference liquid 20 into the water sample being analyzed has three distinct functions: First, because the marker and reference solution is under pressure, it will drive the liquid being analyzed backward out through the inlet 14, which clears the inlet filter 16 of any accumulated debris. Second, because the water sample being analyzed is marked (for example it may be colored with dye) it is made visible as it later passes into the water sample storage capillary 24. Third, the marker and reference solution may have a known calibrating reference characteristic, such as a known pH with which the pH sensor can be calibrated. The frequency of the injection of the marker and reference solution is user-programmable and will probably number about 100 over the duration of operation. The visible markers within the water sample being analyzed serve as index points for the user should it be desired to access a sample of water taken at a specific time after the device has been recovered.

After the liquid being analyzed passes through the wells 32 in the microfluidic manifold assembly 18 which contain the individual water condition sensors 22, the water sample being analyzed leaves the microfluidic manifold assembly 18 and enters the long transparent water sample storage capillary 24. Capillary 24 is sized based on the following criteria:

1) the total length of time the water sample monitoring and water sample storage system is to run unattended;
2) the volume of water per hour or per day that it is desired to collect;
3) the amount of spreading out of water samples that is allowable before the water samples are physically collected for laboratory analysis;
4) the overall size of the housing.

The following calculations are exemplary of how the capillary dimensions and the amount of vacuum in the container can be used to determine each of these quantities.

The total sampling time T may be determined by the following formula:

$$T = \frac{8\eta L^3}{R^2 \Delta p}$$

where $\eta$ is the viscosity of the liquid, L is the capillary length, R is the capillary inner radius, and $\Delta p$ is the pressure difference between outside pressure and the vacuum chamber.

Typical values might be:
$\eta$=0.01 poise (water, 20° C.)
L=5×10$^4$ cm=500 meters
R=0.01 cm
$\Delta p$=10$^6$ dynes/cm2 (vacuum inside housing)

Accordingly, the total sampling time, T, is T=2×10$^6$ sec=556 hours=23 days.

The rate of liquid collection in cm$^3$/sec may be calculated by the formula:

$$V = \frac{\pi \Delta p R^4}{8\eta L}$$

A typical rate of liquid collection might be:
V=8×10$^{-6}$ cm$^3$/sec
=28 $\mu$Liters/hour
=0.7 cm$^3$/day Because the inner radius of the capillary tube is raised to the fourth power in the foregoing formula, the inner radius of the capillary tube strongly affects the volume of liquid that may be collected each day.

Capillaries 24 are small bore capillaries of the types commonly used for applications such as capillary electrophoresis and high pressure liquid chromatography. They are typically made of silica but could also be made of metal. A typical range of inner diameter size is 0.01 to 0.1 millimeters.

Due to the fact that the collected samples of water are stored in a continuous column within the water sample storage capillary 24, there is a slow diffusion of the samples of liquid throughout the column. The consequence of this slow diffusion is a gradual blurring of information on exactly when the water samples were taken. There is no loss of the samples of liquid contained within the water sample storage capillary 24; rather, the times at which the water composition may have changed are blurred due to mixing within the continuous column of liquid. It is well known that the liquid contents of a capillary tube remain essentially unmixed while they flow, provided the flow velocity is low enough. It is possible, however, to mathematically analyze the liquid diffusion in fine capillaries. Specifically, the amount of spreading of samples in capillaries is given by the formula:

$$\Delta T = 2.68 \sqrt{\frac{\eta L^2}{2 D_i \Delta p}}$$

where $D_i$ is the diffusion coefficient for the ions or particles in question through water. Using the values given above, $\Delta T = 0.83$ hours of blurring.

The total size of the housing 12 is primarily determined by the requirement to spool the entire water sample storage capillary 24 inside the evacuated sealed housing 12. In the preferred embodiment, the water sample storage capillary 24 has a minimum radius of bending of about 1". When a 1½" bending radius is used to wind the water sample storage capillary 24 on 3" diameter spools 34, about 2000 turns are needed to place 500 meters of capillary 24 on a 3" diameter spool 34. Given an outside diameter of 0.04 cm, about 100 turns can be placed into a 2" thick vacuum chamber on a 3" diameter spool. About 20 layers of capillary 24 on the spool 34 are needed to fit all of the capillary 24 in the housing 12. This results in a spool outer diameter of about 3.8" for a 23-day sampling duration. For longer periods of unattended operation the housing 12 must be larger, and for shorter periods of operation, smaller housings 12 may be employed.

When the sampling period is over, the system 10 is retrieved from the field where it has been deployed, and the external plug (not shown) reinstalled in the inlet 14 to discontinue water intake. The activity of the microprocessor assembly 26 is halted and the sensor data is uploaded from its nonvolatile memory to an external computer where it is processed into a more usable form such as a table or graph. It is envisioned that certain sensor readings (or mathematical combinations of them) can be correlated and used to decide whether certain samples of water merit a full laboratory analysis. It can be further determined where to break the capillary 24 open to retrieve a particular portion of the sampled water. The selected sample can then be located in the capillary 24 with a precision of $\Delta T = 0.83$ hours, as shown in the calculation above.

Through the use of a glass capillary to store the water samples, it is possible to cross-reference the samples with the timed sensor readings regardless of the factors that might influence the capillary flow rate, such as clogging by debris or variation in the viscosity of water with temperature. The periodic injection of marker liquid also permits preservation of sample timing, despite the variation of fill rate with temperature, bubble formation, etc.

The transparency of a glass capillary may also allow automated counting and searching for samples in the linear record maintained within the capillary 24 by looking for colored bands. The capillary need not be merely an inert container; some types of biochemical analysis within the device may be enabled by the transparency of the capillaries, such as fluorescence spectroscopy detection of DNA. Also, some analyses may be enabled by functionalizing the inner wall of the capillaries for the purpose of binding and preserving biological debris such as cell proteins or DNA fragments. This would allow the monitoring device to function as an integrating collector, which could be flushed with a solvent and concentrated in the laboratory for a high-sensitivity analysis. The capability of providing automated, indexed sequential access to the column of stored water samples is a feature of this invention. Analogous to a disk drive on a computer, more data than can be stored in RAM can be saved, but accessed more slowly and in sequential fashion.

The combination of electronic sensors with stored physical samples permits corroboration of readings. There is a distinct advantage in being able to consult an electronic record quickly to spot possibly interesting points in the water sample history, and thereby minimize the laborious chemical analysis of all of the water contained in the sampling device. In this sense, system combines the best features of integrating samplers, which never miss a chemical change in their environment, and grab samplers which take samples only periodically or when triggered by a predetermined sensor level.

In an alternative embodiment, system 10 may also include a low power transmitter to enable remote real time monitoring of the output of the electronic water condition sensors 22. Such low power transmitters are well known to those of ordinary skill in the art.

While the foregoing invention has been described in terms of its preferred embodiment, it will be understood by those of ordinary skill in the art that other systems incorporating the principles of the disclosed invention may be constructed. Such other systems shall be included within the scope and meaning of the appended claims.

what is claimed is:

1. A liquid sample acquisition storage device comprising:
   an evacuated housing, said housing having an inlet in liquid connection with a microfluidic manifold assembly, said microfluidic manifold assembly containing at least one signal producing liquid analyzing sensor;
   a reservoir in liquid connection with said microfluidic manifold assembly;
   a microprocessor assembly having means for both storing the signals obtained from said signal producing liquid analyzing sensor and controlling the flow of a marker solution from a pressurized source of marker solution into the liquid sample; and
   at least one capillary for storing liquid samples.

2. The liquid sample acquisition and storage device as defined in claim 1, further including a filter in said inlet.

3. The liquid sample acquisition and storage device as defined in claim 1, wherein said microfluidic manifold assembly further includes at least one well in which said at least one signal producing liquid analyzing sensor is positioned.

4. The liquid sample acquisition and storage device as defined in claim 1, wherein said signal producing liquid analyzing sensor is selected from a group including electrochemical, optical, acoustical, electrical or magnetic sensors.

5. The liquid sample acquisition and storage device as defined in claim 1, wherein said liquid is analyzed for temperature, pressure, pH, the presence of chloride ions, the presence of K+ ions, and the presence of $NO_3$ ions.

6. The liquid sample acquisition and storage device as defined in claim 1, wherein said signal producing liquid analyzing sensors include at least one biologically active sensor.

7. The liquid sample acquisition and storage device as defined in claim 6, wherein said at least one biologically active sensor is a surface acoustic wave resonator whose face is sensitized with either antigens or DNA fragments.

8. The liquid sample acquisition and storage device as defined in claim 1, wherein said reservoir is constructed and arranged to flush out said inlet of said evacuated housing.

9. The liquid sample acquisition and storage device of the present invention as defined in claim 1, wherein said reservoir is filled with a reference liquid of known composition to pass through said microfluidic manifold assembly to said signal producing liquid analyzing sensor to calibrate said signal producing liquid analyzing sensor.

10. The liquid sample acquisition and storage device as defined in claim 1, wherein said capillary is stored on a reel within said housing.

11. The liquid sample acquisition and storage device as defined in claim 1 wherein the microprocessor assembly is programmed to correlate the stored signals in said microprocessor assembly with a sample stored in said evacuated capillary.

12. The liquid sample acquisition and storage device as defined in claim 1, wherein said evacuated capillary permits the examination of the stored liquid samples using fluorescence spectroscopy.

13. The liquid sample acquisition and storage device as defined in claim 1, wherein the entry of liquid into said evacuated housing is controlled by said microprocessor assembly.

14. The liquid sample acquisition and storage device as defined in claim 1, further including means for real time monitoring of the output of said signal producing liquid condition sensors.

15. A method for monitoring and storing liquid samples at a remote location comprising the steps of:

drawing a flow of liquid into a sealed housing by vacuum within the housing;

directing said flow of liquid through a microfluidic manifold assembly;

contacting said liquid with at least one signal producing liquid condition sensor;

storing the signals produced by said at least one signal producing liquid condition sensor in a microprocessor assembly; and directing said liquid samples and a marker liquid into a capillary.

16. The method of claim 15, further comprising the step of injecting a marker solution into said flow of liquid to separate samples of said liquid.

17. The method of claim 16, wherein said marker solution is also used to flush out said inlet of said evacuated housing.

18. The method of claim 16, wherein said marker solution is used to calibrate said signal producing liquid condition sensors.

19. The method of claim 16, wherein said evacuated capillary is stored on a reel within said sealed housing.

20. The method of claim 16, wherein the insertion of said marker solution into said flow of liquid is triggered by the elapse of a specified time period.

21. The method of claim 16, wherein the insertion of said marker solution into the flow of liquid is triggered by exceeding a predetermined signal level produced by said at least one signal producing liquid condition sensor.

22. The method of claim 15, wherein said signal producing liquid condition sensors are selected from a group including electrochemical, optical, acoustical, electrical or magnetic sensors.

23. The method of claim 15, wherein said liquid conditions monitored are selected from a group including temperature, pressure, pH, the presence of chloride ions, the presence of K+ ions, and the presence of $NO_3$ ions.

24. The method of claim 15, wherein said signal producing liquid condition sensors include at least one biologically active sensor.

25. The method of claim 15, wherein the step of drawing the liquid into said housing is continuous.

26. The method of claim 15, further comprising the step of correlating the stored signals in said microprocessor assembly with said liquid samples stored in the capillary.

27. The method of claim 15, further comprising the use of the stored signals to identify regions of the liquid in the capillary.

28. The method of claim 15, wherein said evacuated capillary permits the examination of said stored liquid samples using fluorescence spectroscopy.

29. The method of claim 15, further comprising the step of controlling the entry of said flow of liquid into the housing with the microprocessor assembly.

30. The method of claim 20, further comprising the step of monitoring, in real time, the output of said signal producing liquid condition sensors.

* * * * *